United States Patent
Bonner et al.

(10) Patent No.: US 10,238,865 B2
(45) Date of Patent: Mar. 26, 2019

(54) ELECTRODE FIXATION IN INTERVENTIONAL MEDICAL SYSTEMS

(71) Applicant: Medtronic, Inc., Minneapolis, MN (US)

(72) Inventors: Matthew D Bonner, Plymouth, MN (US); Raymond W Usher, Coon Rapids, MN (US); Teresa A Whitman, Dayton, MN (US); Jean M Carver, Blaine, MN (US); Kathryn Hilpisch, Cottage Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 15/287,122

(22) Filed: Oct. 6, 2016

(65) Prior Publication Data
US 2018/0099138 A1    Apr. 12, 2018

(51) Int. Cl.
*A61N 1/05* (2006.01)
*A61N 1/375* (2006.01)
*A61N 1/372* (2006.01)
*A61B 17/34* (2006.01)

(52) U.S. Cl.
CPC .......... *A61N 1/059* (2013.01); *A61B 17/3468* (2013.01); *A61N 1/0573* (2013.01); *A61N 1/3756* (2013.01); *A61N 1/37205* (2013.01); *A61N 1/37518* (2017.08)

(58) Field of Classification Search
CPC ................ A61N 1/0592; A61N 1/3624; A61N 1/37205; A61N 1/3756; A61N 1/375; A61N 17/3468; A61N 1/059; A61N 1/37518; A61N 1/0573; A61B 17/3468; A61B 2017/00044
See application file for complete search history.

(56) References Cited

U.S. PATENT DOCUMENTS

| | | |
|---|---|---|
| 3,814,104 A | 6/1974 | Irnich et al. |
| 3,943,936 A | 3/1976 | Rasor et al. |
| 4,103,690 A | 8/1978 | Harris |

(Continued)

OTHER PUBLICATIONS www.mana-tech.com/factsheets/HomerMammalok.pdf, Anglotech (PBN Medicals Denmark A/S), 1 page.
(Continued)

*Primary Examiner* — Catherine M Voorhees

(57) ABSTRACT

An implantable medical device assembly includes a mounting structure, an electrode protruding from a surface of the structure, between opposing sides thereof, and tissue-penetrating fixation tines, each extending from a corresponding shoulder of the structure surface, adjacent to the opposing sides. In a relaxed condition, each tine extends away from the surface and then bends toward a proximal end of the structure and back toward the surface. In an extended condition, each tine bends toward a distal end of the structure and extends along the corresponding shoulder. A holding member of a delivery tool has opposing sidewalls defining a cavity, wherein each sidewall includes a rail-like edge that fits in sliding engagement with a corresponding shoulder, to deform a corresponding tine into the extended condition, when an operator passes the assembly into the cavity. Applying a push force, to move the assembly back out form the cavity, releases the tines.

17 Claims, 8 Drawing Sheets

(56) References Cited

U.S. PATENT DOCUMENTS

| | | |
|---|---|---|
| 4,142,530 A | 3/1979 | Wittkampf |
| 4,357,946 A | 11/1982 | Dutcher et al. |
| 4,607,644 A | 8/1986 | Pohndorf |
| 4,913,164 A | 4/1990 | Greene et al. |
| 5,050,600 A | 9/1991 | Parks |
| 5,300,107 A | 4/1994 | Stokes et al. |
| 5,443,492 A | 8/1995 | Stokes et al. |
| 5,571,162 A | 11/1996 | Lin |
| 5,871,532 A | 2/1999 | Schroeppel |
| 6,510,347 B2 | 1/2003 | Borkan |
| 7,085,606 B2 | 8/2006 | Flach et al. |
| 7,270,669 B1 | 9/2007 | Sra |
| 7,610,104 B2 | 10/2009 | Kaplan et al. |
| 7,647,109 B2 | 1/2010 | Hastings et al. |
| 7,715,924 B2 * | 5/2010 | Rezai ............ G06F 9/4436 607/117 |
| 8,478,431 B2 | 7/2013 | Griswold et al. |
| 8,532,790 B2 | 9/2013 | Griswold |
| 2004/0176830 A1 | 9/2004 | Fang |
| 2006/0247753 A1 | 11/2006 | Wenger et al. |
| 2011/0251661 A1 | 10/2011 | Fifer et al. |
| 2011/0251662 A1 | 10/2011 | Griswold et al. |
| 2012/0172690 A1 * | 7/2012 | Anderson ............ A61N 1/0573 600/347 |
| 2015/0039069 A1 | 2/2015 | Rys et al. |
| 2015/0045868 A1 | 2/2015 | Bonner et al. |
| 2015/0051682 A1 | 2/2015 | Schmidt et al. |
| 2015/0273212 A1 | 10/2015 | Berthiaume et al. |
| 2016/0059003 A1 | 3/2016 | Eggen et al. |

OTHER PUBLICATIONS

U.S. Registration No. H356 issued to Stokes et al. published Nov. 3, 1987, 7 pages.

C00010730.WOU2 (PCT/US22017/055553) PCT Notification of Transmittal of the International Search Report and the Written Opinion of the International Searching Authority, dated Jan. 8, 2018, 13 pages.

* cited by examiner

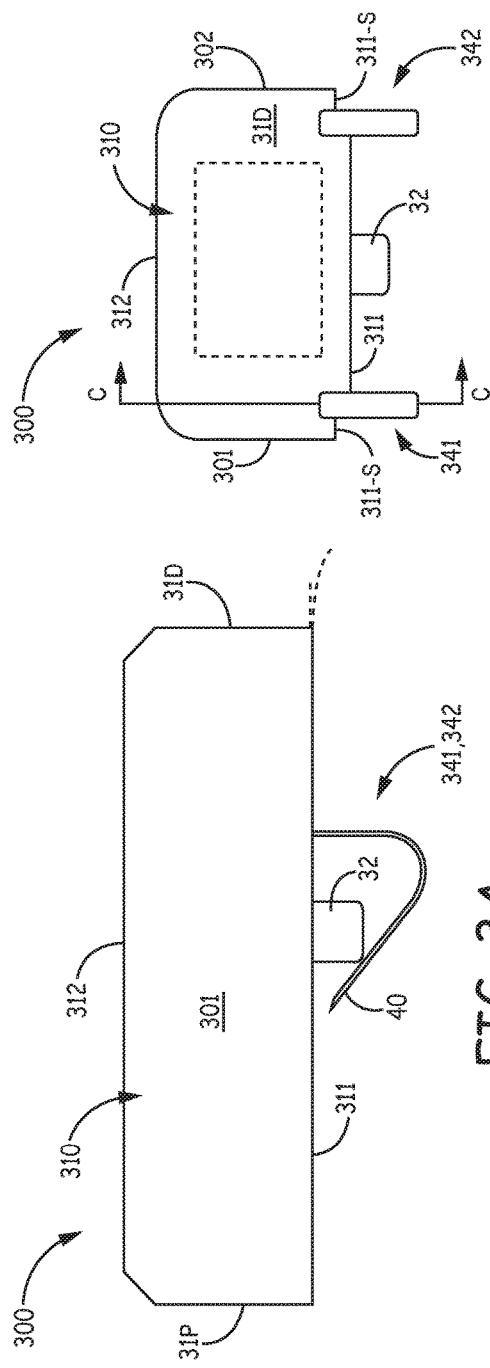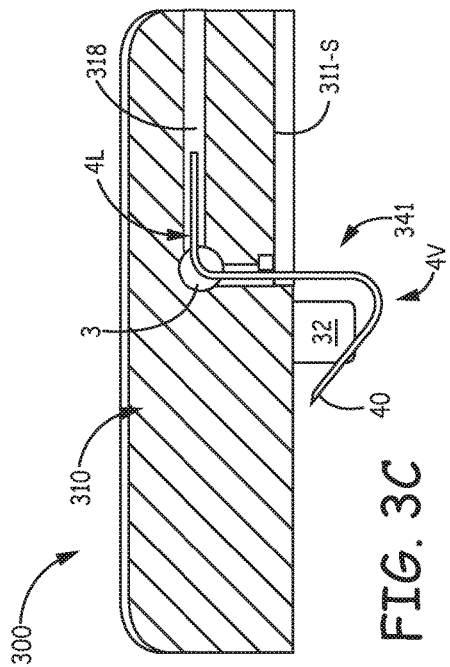

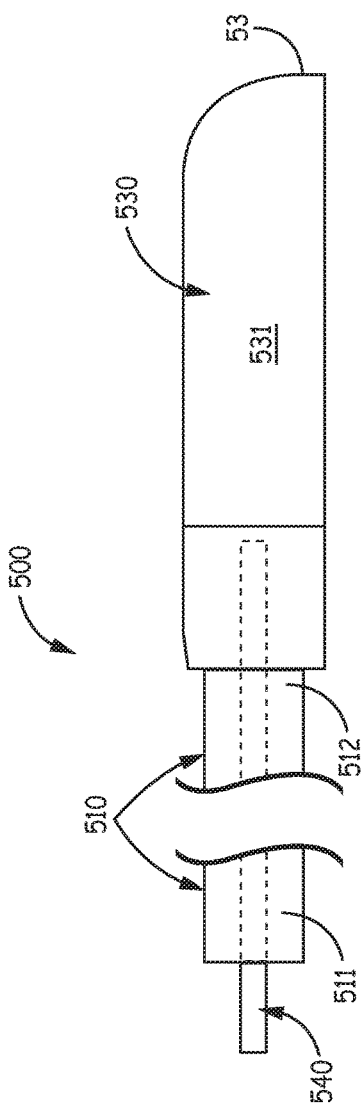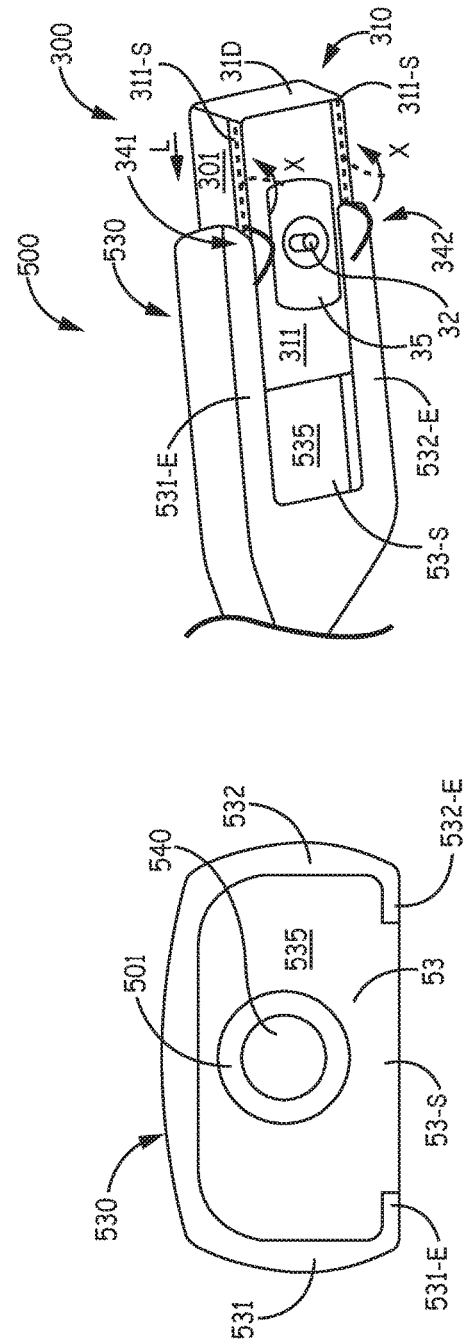

ELECTRODE FIXATION IN INTERVENTIONAL MEDICAL SYSTEMS

TECHNICAL FIELD

The present invention pertains to interventional medical systems, and, more specifically, to implantable electrode fixation at a stimulation site.

BACKGROUND

An implantable medical device, for the delivery of stimulation therapy, may include an electrode and a fixation component configured to hold the electrode in intimate contact with tissue at a stimulation site. One type of such a device may be a traditional implantable cardiac pacemaker that includes a pulse generator and a pacing electrode coupled to the generator by an elongate insulated lead wire. The pulse generator is typically implanted in a subcutaneous pocket, remote from the heart, with the lead wire extending therefrom to a pacing site where the electrode is positioned. Another type of implantable medical device may be one wholly contained within a relatively compact package for implant in close proximity to the pacing site. FIG. 1 illustrates such a device 100 including an hermetically sealed housing 105, preferably formed from a biocompatible and biostable metal such as titanium, that contains an electronic controller and associated power source (not shown), to which at least one electrode 111 is coupled, for example, by a hermetic feedthrough assembly (not shown).

With further reference to FIG. 1, device 100 has been deployed by an operator via a delivery tool 200, which the operator has maneuvered up through the inferior vena cava IVC and across the right atrium RA into the right ventricle RV. The deployed device 100 is shown fixed at the pacing site by a fixation member 115 thereof, for example, including tissue-penetrating tines that surround electrode 111 and secure electrode 111 in intimate contact with tissue at the site. Further description of a suitable construction for device fixation member 115 may be found in the co-pending and commonly assigned United States Patent Application having the pre-grant publication number 2012/0172690 A1.

An alternative pacing site may be located on an epicardial surface of the heart, for example, on the left side of the heart for the application of pacing therapy to treat heart failure. FIG. 2 is a schematic showing an access site A for creating a passageway between a patient's diaphragm 19 and xiphoid process 20 of sternum 13, for example, to implant a pacing electrode on an epicardial surface 6 of the patient's heart, which is enclosed within the pericardial sac 15. After making a superficial incision, an operator may open a passageway between diaphragmatic attachments 18 and diaphragm 19 by using blunt dissection tools and techniques that are known in the art. Then, the operator may employ a piercing tool to pass a guide wire through the pericardial sac 15, also according to methods known in the art. The operator may use fluoroscopic guidance to position a distal portion of the guide wire along a portion of epicardial surface 6, at which a target site is located, and then pass a guiding sheath over the positioned guide wire. The guiding sheath then serves as a conduit for delivery of the implantable electrode to the target site. In this context, to deliver and then fix, or secure the implantable electrode at an epicardial site, there is a need for new configurations of interventional systems and associated implantable device assemblies.

SUMMARY

An implantable medical device assembly, according to some embodiments of the present invention, includes: a mounting structure having opposing sides that define a width thereof, proximal and distal ends that define a length thereof, and a surface that extends between the opposing sides and proximal and distal ends, and that has shoulders formed therein, each being adjacent a corresponding side of the structure; an electrode being approximately centered between the opposing sides and protruding from the surface of the mounting structure; and first and second tissue-penetrating fixation tines, each of which extends from a corresponding shoulder of the mounting structure surface. Each tine is elastically deformable from a relaxed condition to an extended condition, wherein, in the relaxed condition, each tine extends away from the mounting structure surface and then bends toward the proximal end of the structure and back toward the surface so that a piercing tip of each tine is located proximal to the electrode, and wherein, in the extended condition, each tine bends toward the distal end of the structure and extends along the corresponding shoulder of the structure.

In some embodiments, each fixation tine is a component formed from a super-elastic wire, and the component may include a pre-formed L-shaped segment and a pre-formed V-shaped segment terminated by the piercing tip. The segments may bend in opposite directions but in a single plane, the same for both. In the above described assembly, the mounting structure may include first and second internal channels, wherein the L-shaped segment of each fixation tine is mounted in a corresponding internal channel so that the corresponding V-shaped segment extends away from the corresponding shoulder.

An interventional medical system of the present invention, according to some embodiments, includes the above described device assembly and a delivery tool, wherein the delivery tool includes a holding member with opposing sidewalls defining a cavity sized to hold the device assembly mounting structure therein, and wherein each sidewall includes a rail-like edge that fits in sliding engagement with a corresponding shoulder of the mounting structure and deforms a corresponding fixation tine of the device assembly into the extended condition. According to some methods of the present invention, an operator passes the proximal end of the mounting structure through a distal opening of the holding member cavity, until the rail-like edges come into sliding engagement with respective shoulders of the mounting structure; and then the operator continues to pass the mounting structure into the cavity, to load the device assembly therein, so that each engaged rail-like edge elastically deforms the corresponding tissue-penetrating fixation tine from a relaxed condition to an extended condition. After the operator positions the holding member and loaded device assembly at a stimulation site, for example, on an epicardial surface of a patient's heart, the operator can release the fixation tines of the device assembly from the extended condition, to engage with tissue at the site, by applying a push force against the mounting structure of the device assembly.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals/letters denote like elements, and:

FIGS. 3A-B are a plan view and an end view of an implantable medical device assembly, according to some embodiments;

FIG. 3C is a cross-section view through section line C-C of FIG. 3B, according to some embodiments;

FIGS. 5A-B are a plan view and an end view of a delivery tool which may be included together with embodiments of device assemblies in an interventional medical system, according to some embodiments;

FIG. 5C is a perspective view of a portion of the delivery tool and the device assembly together, according to some embodiments and methods;

DETAILED DESCRIPTION

Figure 1:
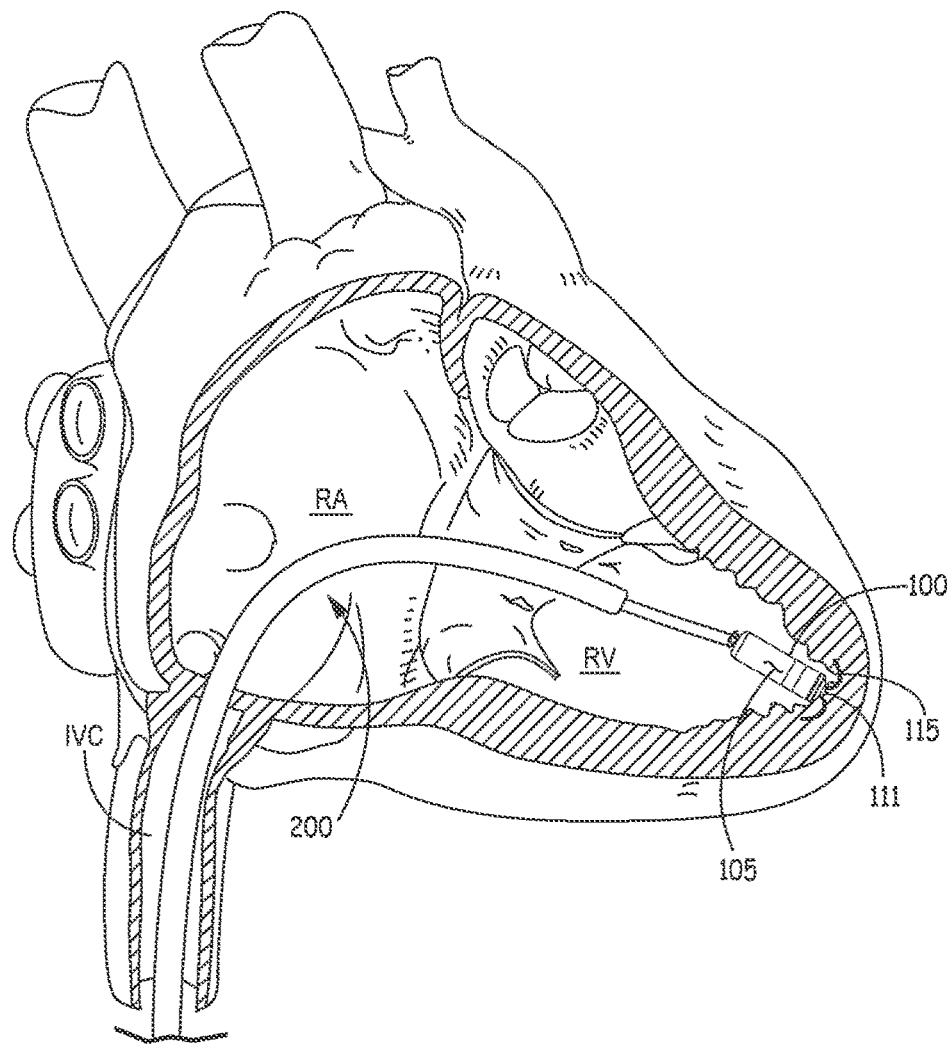
FIG. 1 is a schematic showing an exemplary implant of a relatively compact medical device.

The following detailed description is exemplary in nature and is not intended to limit the scope, applicability, or configuration of the invention in any way. Rather, the following description provides practical examples, and those skilled in the art will recognize that some of the examples may have suitable alternatives.

FIGS. 3A-B are a plan view and an end view of an implantable medical device assembly 300, according to some embodiments. FIGS. 3A-B illustrate device assembly 300 including a mounting structure 310 having a length defined from a proximal end 31P to a distal end 31D thereof, a thickness defined from a first surface 311 to a second surface 312 thereof, and a width defined from a first side 301 to a second side 302 thereof. FIGS. 3A-B further illustrate assembly 300 including an electrode 32 protruding from first surface 311 of structure 310, and first and second tissue-penetrating fixation tines 341, 342 located on either side of electrode 32, which may be approximately centered therebetween. According to preferred embodiments, tines 341, 342 are formed from a super-elastic material and are configured to secure electrode 32, in intimate tissue contact, at a stimulation site on an epicardial surface of a patient's heart. To conform to the epicardial surface, first surface 311, being that which confronts the epicardial surface, preferably has a concavity, for example, with a radius of curvature (indicated with dashed lines in FIG. 3A) of between about 1 inch and 6 inches, formed therein. According to one exemplary embodiment, the concavity of surface 311 is centered on mounting structure 310 and has a radius of approximately 3.5 inches set into surface 311 by about 0.015 inch, wherein electrode 32 is located on a centerline of the concavity.

In some embodiments, when device assembly 300 forms a relatively compact implantable medical device, for example, similar to device 100 described above in conjunction with FIG. 1, mounting structure 310 defines a hermetically sealed enclosure (indicated with dashed lines in FIG. 3B), which is sized to hold an electronic controller and associated power source for coupling to electrode 32, for example, via a hermetically sealed feedthrough assembly like that known to those skilled in the art. In these embodiments, as well as in others, structure 310 may be formed from a biocompatible and biostable metal, such as titanium, in combination with an overlay of a biocompatible and biostable polymer, such as parylene, polyimide, or urethane, for electrical isolation. Electrode 32 may be constructed from any suitable material and by any suitable method known to those skilled in the art of medical electrical cardiac pacing.

With further reference to FIG. 3B, mounting structure 310 includes shoulders 311-S formed in first surface 311, wherein each shoulder 311-S is aligned along the length of structure 310 and located adjacent a corresponding side 301, 302 of structure 310, and wherein each tine 341, 342 extends away from a corresponding shoulder 311-S. Each tine 341, 342 includes a piercing tip 40, and FIG. 3A shows tines 341, 342 in a relaxed condition, bending toward proximal end 31P and first surface 311 of structure 310, so that each piercing tip 40 is located proximal to electrode 32. Each tine 341, 342 may be secured to structure 310 by extending within a corresponding internal channel 318 thereof, each of which is located distal to electrode 32, for example, as shown in FIG. 3C, which is a cross-section view through section line C-C of FIG. 3B, according to some embodiments. FIG. 3C illustrates tine 341 including a pre-formed L-shaped segment 4L, which extends within, and interlocks with internal channel 318, and mounting structure 310 including a cross hole 3 (which may extend from first side 301) in communication with channel 318 to receive injection of an adhesive filler that further secures segment 4L in channel 318. Alternately, or in addition, auxiliary mechanical interlocking between pre-formed L-shaped segment 4L and channel 318 may be included. FIG. 3C further illustrates tine 341 including a pre-formed V-shaped segment 4V, which extends from L-shaped segment 4L outside channel 318 and away from shoulder 311-S to define the above-described relaxed condition of tine 341. It should be understood that tine 342, according to the illustrated embodiment, also includes pre-formed L-shaped and V-shaped segments 4L, 4V that extend inside and outside, respectively, a corresponding channel 318 located adjacent to second side 302 of structure. However, according to alternate embodiments, in which the means for mounting tines 341, 342 is varied, what is herein designated as the L-shaped segment 4L of the illustrated embodiment can be pre-formed into any other suitable shape that conforms to alternate mounting means.

Figure 4A:
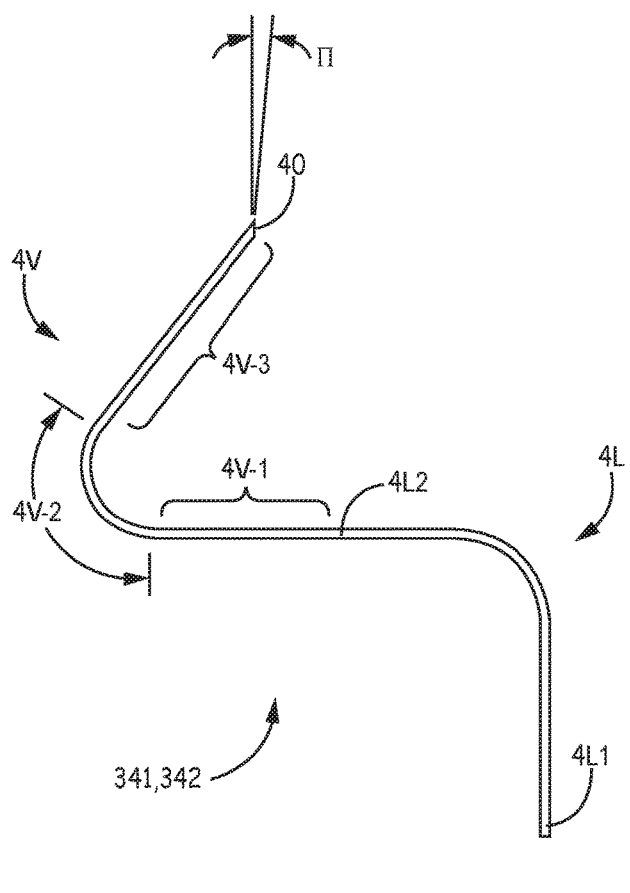
FIGS. 4A-B are a plan view and an end view of a tissue-penetrating tine component, according to some embodiments.

FIG. 4A is a plan view of either of tissue-penetrating fixation tines 341, 342 as a separate component from assembly 300, according to some embodiments. FIG. 4A illustrates tine 341, 342 including the aforementioned pre-formed L-shaped and V-shaped segments 4L, 4V, wherein L-shaped segment 4L extends from a first end 4L1 thereof to a second end 4L2 thereof around a bend that encloses a 90 degree angle, and V-shaped segment 4V extends from second end 4L2 of L-shaped segment 4L to piercing tip 40. FIG. 4A further illustrates V-shaped segment 4V bending in an opposite direction from L-shaped segment 4L, and including a first, relatively straight, portion 4V-1, a second, arched, portion 4V-2, and a third, relatively straight, portion 4V-3, wherein second portion 4V-2 connects first and third portions 4V-1, 4V-3, and third portion 4V-3 is terminated by piercing tip 40. A length of third portion 4V-3, for example, about 0.12 inch, sets a depth to which each tine 341, 342 can 'bite' into tissue at an implant site; and a length of second portion 4V-2, for example, about 0.08 inch around a radius of about 0.03 inch, adds a bit of depth to the bite and determines how much tissue is encompassed in the 'bite' of each tine 341, 342. The release of tines 341, 342 for 'biting' is described in greater detail below, in conjunction with FIG. 7.

Figure 4B:
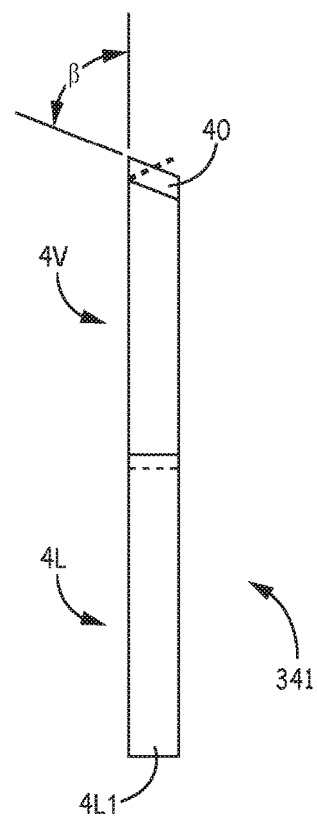

FIG. 4B is an end view of tine component 341, and with reference to FIG. 4B in conjunction with FIG. 4A, each tine component 341, 342 has a generally rectangular axial cross-section that is uniform along both segments 4L, 4V, sans piercing tip 40, wherein a single plane in which both segments 4L, 4V bend is orthogonal to longer sides of the axial cross-section. According to an exemplary embodiment, tine components 341, 342 may be formed from a rolled Nitinol wire (e.g., having a diameter of approximately 0.012 inch, prior to rolling), and piercing tip 40 is formed by a first angled surface cut in one of the longer sides of the axial cross-section, according to an angle $\pi$ (FIG. 4A), for example, of about 25 degrees. Each of tine components may also include a second angled surface cut into one of the shorter sides of the axial cross-section, according to an angle $\beta$ (FIG. 4B), for example, of about 60 degrees, wherein, with further reference to FIG. 4B, in conjunction with the end view of FIG. 3B, the second angled surfaces of tines 341, 342 face generally toward one another in assembly 300, such that the dashed line in FIG. 4B represents the second angled surface of tine 342.

V-shaped segment 4V of each fixation tine 341, 342 is elastically deformable from the illustrated relaxed condition to an extended condition, in which each segment 4V bends toward distal end 31D of structure 310 and extends along the corresponding shoulder 311-S, for example, as described below in conjunction with FIGS. 5C and 6. Tines 341, 342 may be held in the extended condition until an operator positions assembly 300 in proximity to a stimulation site, after which the operator may release tines 341, 342 from the extended condition so that piercing tips 40 'bite' into tissue adjacent the site, thereby securing electrode 32 in intimate tissue contact for stimulation therapy. FIGS. 5A-B are a plan view and an end view of a delivery tool 500, which may be employed by the operator to hold device assembly 300, with tines 341, 342 in the extended position, and to position assembly 300, and then to release tines 341, 342 to secure electrode 32, according to some embodiments of interventional medical systems.

Figure 2:
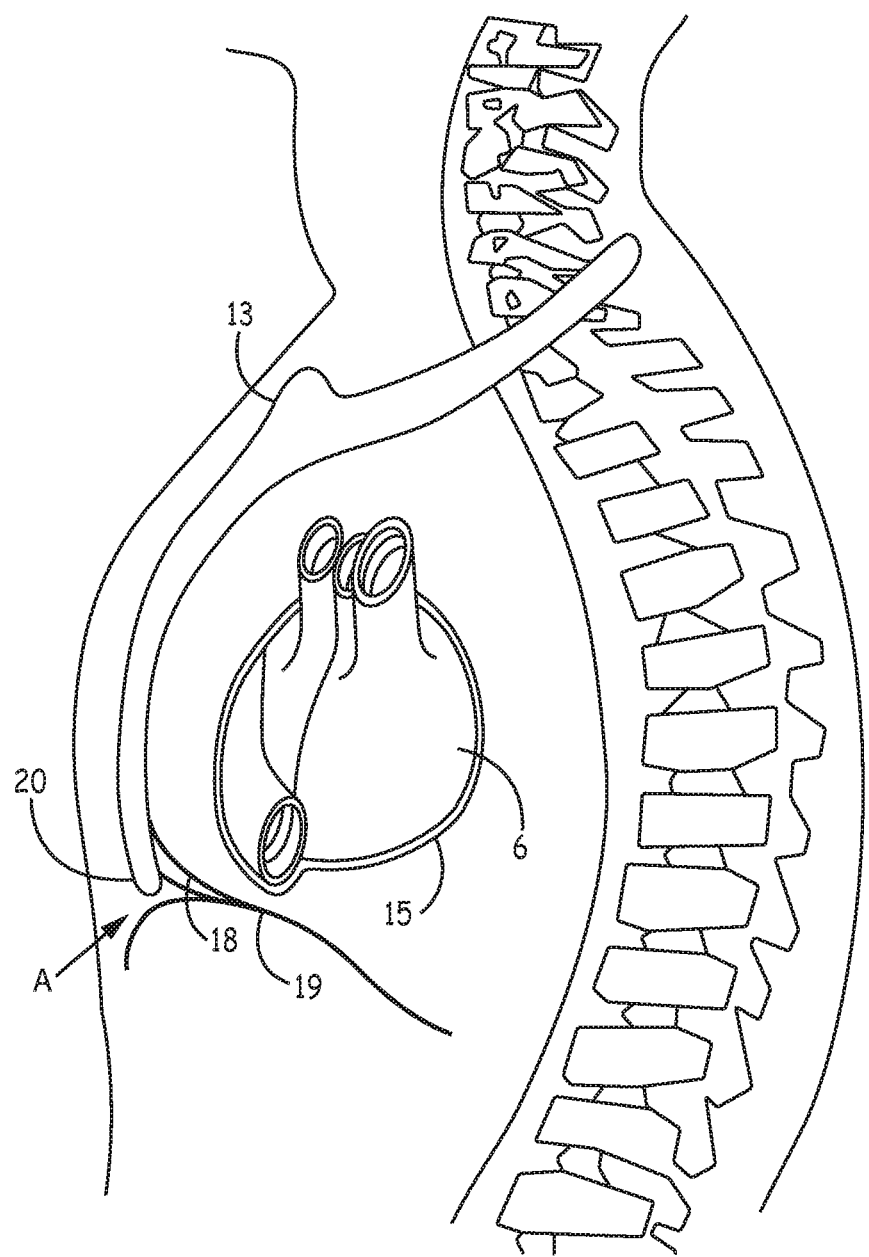
FIG. 2 is a schematic depicting a sub-sternal access site through which an implantable electrode may be passed for securing to an epicardial surface of a patient's heart.

FIGS. 5A-B illustrate delivery tool 500 including an elongate shaft 510 and a holding member 530 attached to a distal end 512 of shaft 510, wherein first and second opposing sidewalls 531, 532 of holding member 530 define a cavity 535 therebetween, which is sized to hold device assembly 300 therein. The end view of FIG. 5B is looking into a distal opening 53 of cavity 535, which may be sized to receive passage of device assembly 300 therethrough, for example, as shown in the perspective view of FIG. 5C. FIG. 5B illustrates each holding member sidewall 531, 532 including a rail-like edge 531-E, 532-E configured to fit in sliding engagement with a corresponding shoulder 311-S of device assembly mounting structure 310 (FIG. 3B), for example, as an operator passes proximal end 31P of device assembly mounting structure 310 into holding member cavity 535, through distal opening 53 thereof. Thus, with reference to FIG. 5C, as the operator continues to pass mounting structure 310 into cavity 535, per arrow L, to load device assembly 300 therein, each engaged rail-like edge 531-E, 532-E elastically deforms the corresponding tissue-penetrating fixation tine 341, 342 from the relaxed condition to the extended condition, according to arrow X and the dashed lines of FIG. 5C. Thus, when assembly 300 is loaded in holding member 530, each tine 341, 342 bends toward distal end 31D of structure 310 and extends along the corresponding shoulder 311-S. With device assembly 300 loaded into holding member 530, the operator can position holding member 530 at an epicardial site, for example, by passing delivery tool 500 into the pericardial space via sub-xiphoid access (e.g., access site A of FIG. 2).

According to an exemplary embodiment, shaft 510 of delivery tool 500, for example, extending over a length of approximately 30 cm to 35 cm, may be formed by a stainless steel braid-reinforced medical grade polymer of one or more appropriate grades of polyether block amide (e.g., PEBAX® 6333 and 7033); and holding member 530 of tool 500 may be formed from an appropriate grade of polyether block amide (e.g., PEBAX® 7233) and include a radiopaque marker bonded thereto, for example, a Platinum/Iridium or gold marker, or a polyamide material with a radiopaque filler, such as Tungsten-filled Vestamid®.

Figure 6:
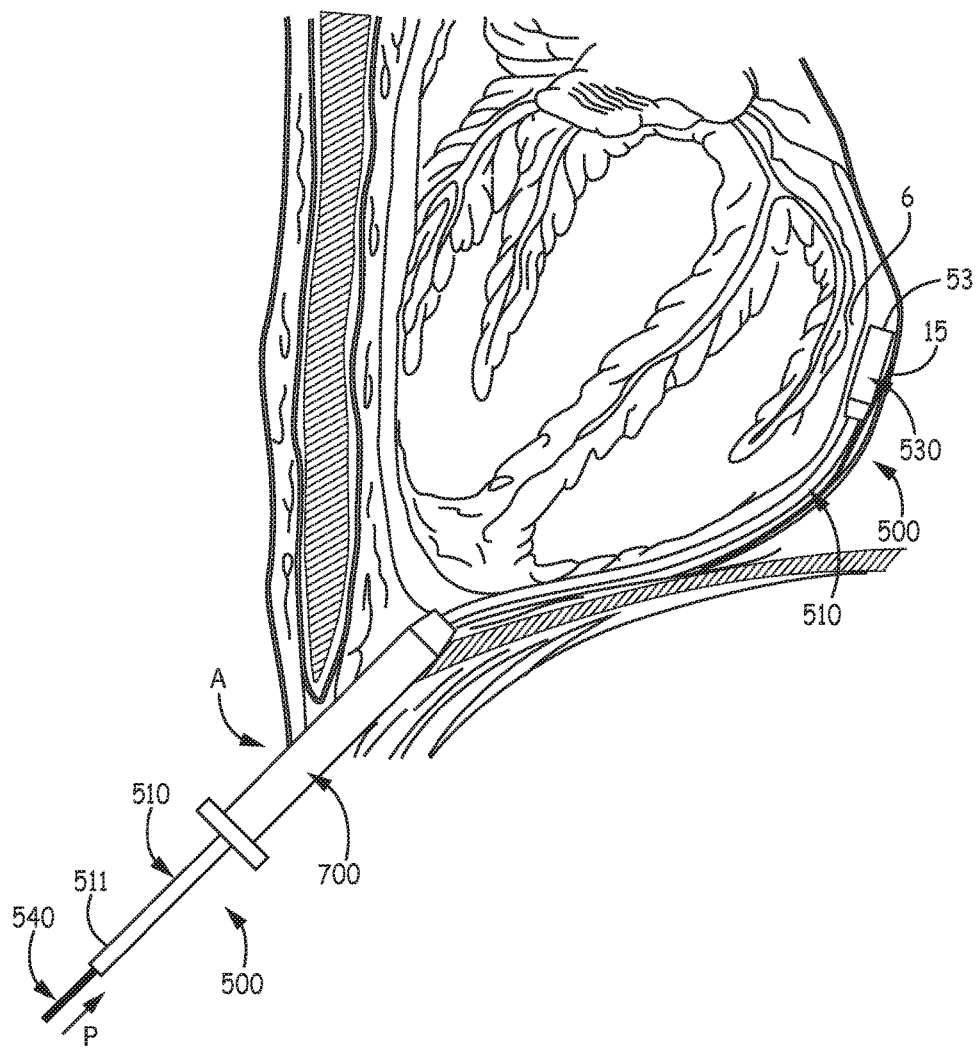
FIG. 6 is a schematic showing the delivery tool positioned for securing an electrode of the medical device assembly at an epicardial site, according to some methods.

FIG. 6 is a schematic showing delivery tool 500 positioned for securing electrode 32 of device assembly 300 at the epicardial site, according to some methods, for example, to provide pacing stimulation. FIG. 6 illustrates a guiding sheath 700 providing a passageway for the insertion of delivery tool 500 into the pericardial space, between epicardial surface 6 and pericardial sac 15, through access site A, which may be formed by any suitable method known in the art, for example, as described above in conjunction with FIG. 2. Fluoroscopic or video monitoring may be employed for guidance in positioning holding member 530.

Figure 7:
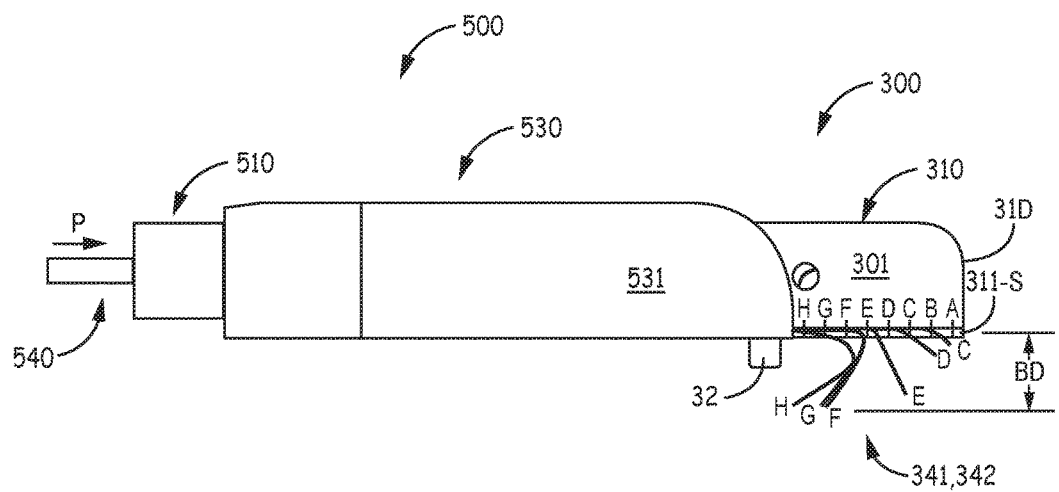
FIG. 7 is a schematic depicting release of tissue-penetrating fixation tines in the interventional medical system, according to some embodiments.

With reference back to FIG. 5B, shaft 510 may include a lumen 501 extending longitudinally from a proximal end 511 to distal end 512 of shaft 510, and being in fluid communication with holding member cavity 535. FIGS. 5A-B and FIG. 6 further illustrate an ejector rod 540 extending in sliding engagement within shaft 510 of delivery tool 500, for example, inserted through lumen 501 by the operator, after positioning holding member 530 and loaded device assembly 300 at the epicardial site and removing the guide wire. According to the illustrated embodiment and some methods, the operator may apply a push force to mounting structure 310 of the loaded and positioned device assembly 300 through rod 540, per arrow P, to move device assembly 300 out through distal opening 53 of cavity 535, thereby releasing fixation tines 341, 342 to 'bite' into tissue at the epicardial site. FIG. 7 is a schematic depicting the release of fixation tines 341, according to some embodiments. FIG. 7 illustrates incremental positions A-H of assembly 300 relative to holding member 530 of delivery tool 500, wherein position A corresponds to device assembly 300 loaded within holding member 530 so that tines 341, 342 are in the extended condition, and positions B-H correspond to the release of tines 341, 342 as piercing tips 40 thereof 'bite' into tissue for securing electrode 32 to a stimulation site. An approximate 'bite' depth BD of tines 341, 342 may be about 0.132 inch (3.3 mm), as dictated by the above disclosed exemplary radius and lengths of tine portions 4V-2 and 4V-3 (FIG. 4A). Once tines 341, 342 are fully engaged with the tissue, for example, being generally at position H, the operator can retract delivery tool 500 from the pericardial space to leave device assembly 300 implanted at the epicardial site.

Figure 8:
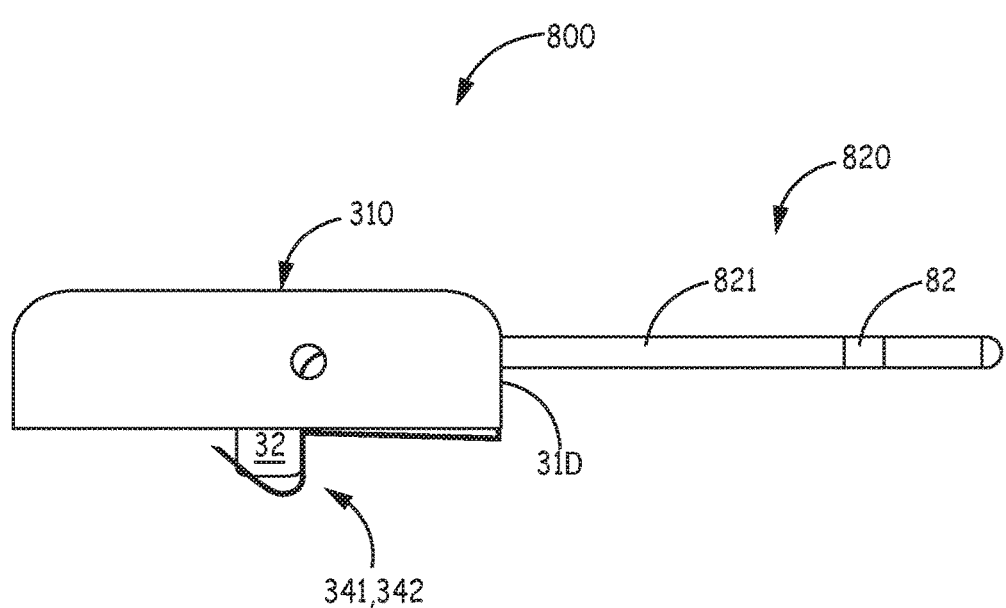
FIG. 8 is a plan view of an exemplary alternate embodiment of the device assembly.

With reference back to FIGS. 5B-C, holding member edges 531-E, 532-E in tool 500 preferably define a longitudinally extending slot 53-S therebetween so that, when device assembly 300 is held in cavity 535, electrode 32 extends through slot 53-S. Thus, electrode 32 can make contact with tissue at the stimulation site prior to the release of tines 341, 342, so that an operator can test electrode function at the site prior to securing electrode 32 to the site, according to some methods. With further reference to FIG. 5C, first surface 311 of device assembly mounting structure 510 is shown including a conductive area 35 surrounding electrode 32, and being isolated therefrom, to form another electrode for bipolar function with electrode 32. Alternately, conductive area 35 is located opposite electrode 32, on second surface 312 of mounting structure 310. According to some exemplary embodiments of device assembly 300, in which mounting structure 310 is formed by a metal and polymer overlay, as described above, conductive area 35 may be formed by removing a portion of the polymer overlay from first surface 311 or second surface 312. According to some alternate embodiments, a device assembly 800, for example, as shown in the plan view of FIG. 8, includes an electrode 82 as part of an elongate electrode subassembly 820 that extends from distal end 31D of mounting structure 310, to form the bipolar pair with electrode 32, in lieu of conductive area 35. In an exemplary embodiment, electrode subassembly 820 includes an insulated conductor 821 electrically coupled, via a hermetically sealed feedthrough (not shown), to the aforementioned controller and power source enclosed within mounting structure 310, wherein electrode 82 is mounted about insulated conductor 821 and electrically coupled thereto. Electrode subassembly 820 may be constructed from any suitable materials and according to any suitable methods known to those skilled in the art of implantable medical electrical leads.

In the foregoing detailed description, the invention has been described with reference to specific embodiments. However, it may be appreciated that various modifications and changes can be made without departing from the scope of the invention as set forth in the appended claims.

The invention claimed is:

1. An implantable medical device assembly comprising:
a mounting structure having a length defined from a proximal end thereof to a distal end thereof, a thickness defined from a first surface thereof to a second surface thereof, and a width defined from a first side thereof to a second side thereof, the mounting structure comprising first and second shoulders formed in the first surface of the structure and aligned along the length of the structure, the first shoulder being adjacent to the first side of the structure, and the second shoulder being adjacent to the second side of the structure;
an electrode protruding from the first surface of the mounting structure; and
first and second tissue-penetrating fixation tines, each tine including a pre-formed V-shaped segment that extends away from a corresponding shoulder of the first surface of the mounting structure, being located on either side of the electrode so that the electrode is approximately centered therebetween, each segment including a piercing tip, and each segment being elastically deformable from a relaxed condition to an extended condition, the relaxed condition being that of the pre-formed V-shape, in which each segment bends toward the proximal end and the first surface of the mounting structure so that each piercing tip is located proximal to the electrode and away from the corresponding shoulder of the mounting structure, and the extended condition being that in which each segment bends toward the distal end of the mounting structure and extends along and within the corresponding shoulder of the mounting structure so that each piercing tip is located distal to the electrode.

2. The assembly of claim 1, wherein:
the mounting structure further comprises first and second internal channels located distal to the electrode; and
each fixation tine further includes a second segment extending in a corresponding channel of the first and second internal channels of the mounting structure.

3. The assembly of claim 2, wherein the second segment of each fixation tine comprises an L-shaped segment.

4. The assembly of claim 1, wherein the first surface of the mounting structure includes a conductive area forming another electrode for bipolar function with the electrode that protrudes from the first surface.

5. The assembly of claim 2, wherein:
each fixation tine has a generally rectangular axial cross-section, the axial cross-section being uniform along the both segments of the tine, sans the piercing tips, and longer sides of each axial cross-section being orthogonal to a single plane in which both segments of each tine bend; and
each fixation tine is oriented so that one of the longer sides of the axial cross section thereof faces toward the second surface of the mounting structure when the pre-formed V-shaped segment of each tine is deformed into the extended condition.

6. The assembly of claim 5, wherein the piercing tip of each fixation tine includes an angled surface, the angled surfaces facing generally toward one another.

7. The assembly of claim 1, wherein the mounting structure defines a hermetically sealed enclosure sized to hold an electronic controller and associated power source for coupling to the electrode.

8. The assembly of claim 7, further comprising an elongate electrode subassembly extending from the distal end of the mounting structure.

9. The assembly of claim 1, wherein the first surface of the mounting structure includes a concavity formed therein, the concavity being centered on the structure, and the electrode being located on a centerline of the concavity.

10. An interventional medical system comprising:
an implantable medical device assembly, the assembly comprising:
a mounting structure having a length defined from a proximal end thereof to a distal end thereof, a thickness defined from a first surface thereof to a second surface thereof, and a width defined from a first side thereof to a second side thereof, the mounting structure comprising first and second shoulders formed in the first surface of the structure and aligned along the length of the structure, the first shoulder being adjacent to the first side of the structure, and the second shoulder being adjacent to the second side of the structure;
an electrode protruding from the first surface of the mounting structure; and
first and second tissue-penetrating fixation tines, each tine including a pre-formed V-shaped segment that extends away from a corresponding shoulder of the first surface of the mounting structure, being located on either side of the electrode so that the electrode is approximately centered therebetween, each segment including a piercing tip, and each segment being elastically deformable from a relaxed condition to an extended condition, the relaxed condition being that of the pre-formed V-shape, in which each segment bends toward the proximal end and the first surface of the mounting structure so that each piercing tip is located proximal to the electrode and away from the corresponding shoulder of the mounting structure, and the extended condition being that in which each segment bends toward the distal end of the mounting structure and extends along and within the corresponding shoulder of the mounting structure so that the piercing tip is located distal to the electrode; and a delivery tool comprising:
    an elongate shaft extending from a proximal end thereof to a distal end thereof;
    a holding member attached to the distal end of the shaft, the holding member including first and second opposing sidewalls defining a cavity therebetween, the cavity being sized to hold the device assembly therein, the cavity including a distal opening sized to allow passage of the device assembly therethrough, and each sidewall including a rail-like edge configured to fit in sliding engagement with a corresponding shoulder of the device assembly mounting structure; and
    means for applying a push force to the device assembly mounting structure, when the device assembly is held in the holding member cavity; and
    wherein, when the device assembly is passed into the cavity of the tool holding member through the distal opening thereof, with the rail-like edge of each holding member sidewall engaged with the corresponding shoulder of the mounting structure, the pre-formed V-shaped segment of each fixation tine is deformed into the extended condition by the rail-like edge of the corresponding sidewall.

11. The system of claim 10, wherein the means for applying the push force in the delivery tool comprises an ejector rod slideably engaged within the tool.

12. The system of claim 10, wherein the sidewall rail-like edges of the tool holding member define a longitudinally extending slot therebetween; and, when the device assembly is held in the cavity of the holding member, the electrode of the device assembly extends through the slot.

13. The system of claim 12, wherein the first surface of the device assembly mounting structure includes a conductive area that forms a second electrode for bipolar function with the device assembly electrode; and when the device assembly mounting structure is held in the cavity of the tool holding member, the second electrode is exposed through the slot of the holding member.

14. The system of claim 10, wherein the device assembly further comprises an elongate electrode subassembly extending from the distal end of the mounting structure.

15. An interventional medical system comprising:
an implantable medical device assembly, the assembly comprising:
    a mounting structure having a length defined from a proximal end thereof to a distal end thereof, a thickness defined from a first surface thereof to a second surface thereof, and a width defined from a first side thereof to a second side thereof, the mounting structure comprising first and second shoulders formed in the first surface of the structure and aligned along the length of the structure, the first shoulder being adjacent to the first side of the structure, and the second shoulder being adjacent to the second side of the structure;
    an electrode protruding from the first surface of the mounting structure; and
    first and second tissue-penetrating fixation tines, each tine including a pre-formed V-shaped segment that extends away from a corresponding shoulder of the first surface of the mounting structure, being located on either side of the electrode so that the electrode is approximately centered therebetween, each segment including a piercing tip, and each segment being elastically deformable from a relaxed condition to an extended condition, the relaxed condition being that of the pre-formed V-shape, in which each segment bends toward the proximal end and the first surface of the mounting structure so that each piercing tip is located proximal to the electrode, and the extended condition being that in which each segment bends toward the distal end of the mounting structure and extends along the corresponding shoulder of the mounting structure so that the piercing tip is located distal to the electrode; and a delivery tool comprising:
    an elongate shaft extending from a proximal end thereof to a distal end thereof; and
    a holding member attached to the distal end of the shaft, the holding member including first and second opposing sidewalls defining a cavity therebetween, the cavity being sized to hold the device assembly therein, the cavity including a distal opening sized to allow passage of the device assembly therethrough, and each sidewall including a rail-like edge configured to fit in sliding engagement with a corresponding shoulder of the device assembly mounting structure, the rail-like edges defining a longitudinally extending slot therebetween; and
    wherein, when the device assembly is passed into the cavity of the tool holding member through the distal opening thereof, with the rail-like edge of each holding member sidewall engaged with the corresponding shoulder of the mounting structure, the pre-formed V-shaped segment of each fixation tine is deformed into the extended condition by the rail-like edge of the corresponding sidewall; and
    when the device assembly is held in the cavity of the holding member, the electrode of the device assembly extends through the slot defined by the rail-like edges of the holding member sidewalls.

16. The system of claim 15, wherein the first surface of the device assembly mounting structure includes a conductive area that forms a second electrode for bipolar function with the device assembly electrode; and when the device assembly mounting structure is held in the cavity of the tool holding member, the second electrode is exposed through the slot of the holding member.

17. The system of claim 15, wherein the device assembly further comprises an elongate electrode subassembly extending from the distal end of the mounting structure.

* * * * *